United States Patent [19]

Hay et al.

[11] Patent Number: 5,444,147

[45] Date of Patent: Aug. 22, 1995

[54] CYCLOPROPANE MONOMERS AND POLYMERS DERIVED THEREFROM

[76] Inventors: Allan S. Hay, 5015 Glencairn Ave., Montreal, Quebec H3W 2B3, Canada; Chunping Gao, 3440 Durocher Ave., Apt. 1106, Montreal, Quebec H2X 2E2, Canada

[21] Appl. No.: 242,428

[22] Filed: May 13, 1994

[51] Int. Cl.$^6$ .............................................. C08G 63/02
[52] U.S. Cl. ..................... 528/193; 528/423; 528/194; 585/350; 585/360
[58] Field of Search ................. 585/350, 360; 528/423, 528/193, 194

[56] References Cited

U.S. PATENT DOCUMENTS 5,233,046   8/1993   Hay et al. ............................ 548/257

OTHER PUBLICATIONS

Studies on Chemical Constitution and Insecticidal Activity. XI. Masayuki Hamada, Botyu-Kagaku 21, 22, 1956, (with English Résumé, 28).
Journal of the American Chemical Society, 87:18, Overberger et al, pp. 4119-4124.

*Primary Examiner*—James J. Seidleck
*Assistant Examiner*—Terressa Mosley
*Attorney, Agent, or Firm*—Swabey Ogilvy Renault

[57] ABSTRACT

Hydroxy-substituted-bis-phenyl cyclopropanes of formula (I):

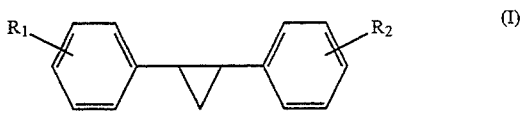

wherein $R_1$ and $R_2$ are selected from H or OH, at least one of $R_1$ and $R_2$ being o, m or p-OH, are useful as monomers to provide cross-linkable polymers useful in fiber reinforced plastics, thermosetting molding compounds, elastomers, advanced composites and other applications; the compounds (I) may be produced by the base catalyzed decomposition of a pyrazoline of formula (II):

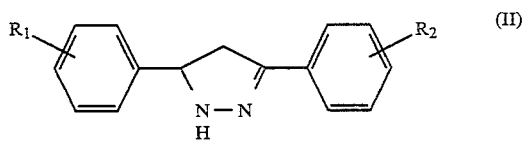

wherein $R_1$ and $R_2$ are as defined hereinbefore.

14 Claims, 5 Drawing Sheets

FIG. 1

Effect of Curing Time on Tg

FIG. 2

Effect of Curing Time on ΔCp at Tg

FIG. 3

Swelling of Cross-linked Polymers

CYCLOPROPANE MONOMERS AND POLYMERS DERIVED THEREFROM

BACKGROUND OF THE INVENTION

1. Field of the Invention

This invention relates to novel cyclopropanes and polymers-derived therefrom, as well as a process for manufacture of the cyclopropanes and a process for manufacture of the polymers.

2. Brief Description of Prior Art

Advanced composite materials are made from combinations of high performance fibers, such as glass, graphite, carbon, silicon carbide or ceramic fibers, arranged in close packed alignment in the polymer as a matrix. Such composite materials provide a combination of strength and modulus superior to that of structural metals and alloys on an equal weight basis. Such composites are, for example, employed in military and commercial aircraft, and space vehicles, as well as in sports equipment, in tennis racquets, shafts for golf clubs and sailboats.

These composite materials are expensive, and so their use is confined to relatively high cost items. On the other hand, even though the raw materials for these advanced composites are expensive, over 70% of the costs associated with such composites result from the processing costs for their manufacture.

In particular, the currently used manufacturing processes produce volatiles during curing of the polymer matrix and such volatiles produce voids in the matrix which act as sites for structural failure. In order to minimize void formation during evolution of volatiles, the cure must be carried out over a long period, under reduced pressure and this manufacturing requirement is a major factor in the production cost.

Cross-linkable polymers are an important class of materials used in fiber reinforced plastics, thermosetting molding compounds, elastomers, coatings, adhesives, ion exchange resins, matrix resins for advanced composites and many other applications. A great deal of effort has been expended on the introduction of reactive functionality into polymers which will act as sites for cross-linking the polymers when heated.

The largest effort has been centered on the synthesis of polymers which contain terminal reactive groups such as acetylene containing moieties. Generally this involves the preparation of oligomers with reactive end groups which can subsequently be thermally chain extended to produce a highly cross-linked polymer matrix. Polymers containing reactive pendent groups have also been synthesized and these polymers have been thermally cured. Polymers containing internal reactive groups, have been less studied. High temperature cross-linkable polymers containing reactive groups such as acetylene, benzocyclobutene, ethylene and epoxide have been investigated, as described in U.S. Pat. No. 5,223,046, Hay et al.

SUMMARY OF THE INVENTION

It is an object of this invention to provide novel cyclopropane monomers useful in the preparation of cross-linkable polymers.

It is a further object of this invention to provide a process for producing the cyclopropane monomers.

It is a still further object of this invention to provide novel polymers based wholly or partly on the cyclopropane monomers.

It is yet a further object of this invention to provide processes for producing the novel polymers.

It is still a further object of the invention to provide novel pyrazolines useful as intermediates or precursors in the manufacture of the cyclopropane monomers.

In accordance with the present invention it has been found that cyclopropane monomers can be incorporated into high molecular weight linear polymers and copolymers which can be cross-linked by heat or photochemical means.

In accordance with one aspect of the invention there is provided a cyclopropane of formula (I):

wherein $R_1$ and $R_2$ are selected from H or OH, at least one of $R_1$ and $R_2$ being o, m or p-OH.

In accordance with another aspect of the invention there is provided a process for producing a cyclopropane of formula (I) as defined hereinbefore comprising base catalyzed decomposition of a pyrazoline of formula (II):

wherein $R_1$ and $R_2$ are as defined above.

In accordance with yet another aspect of the invention there is provided a pyrazoline of formula (II):

wherein $R_1$ and $R_2$ are selected from H or OH, at least one of $R_1$ and $R_2$ being o, m or p-OH.

The pyrazoline of formula (II) is useful as an intermediate for producing the cyclopropanes of formula (I).

In accordance with still another aspect of the invention there is provided a homopolymer or copolymer containing a repeating unit of formula (IV):

(IV)

wherein each ether linkage is in an ortho, meta or para-position, and Ar is a unit derived from a dihalide in which the halogen atoms are readily displaced by phenolic hydroxyl.

DESCRIPTION OF PREFERRED EMBODIMENT i) Cyclopropanes

In the novel cyclopropanes of formula (I), the hydroxyl groups in the definition of $R_1$ and $R_2$ may be in ortho, meta or para-positions.

The cyclopropanes of formula (I) in which one of $R_1$ and $R_2$ is hydrogen are useful as terminators to provide terminal radicals of formula (VIII):

(VIII)

to terminate the polymer chain during homopolymerization or copolymerization.

The cyclopropanes of formula (I) in which $R_1$ and $R_2$ are both hydroxyl groups participate in the homopolymerization or copolymerization to extend the polymer chain.

Cyclopropanes (I) in which $R_1$ and $R_2$ are both hydroxyl in the same positions relative to the cyclopropyl group, for example, both in parapositions, are especially preferred.

ii) Production of Cyclopropanes

The cyclopropanes (I) are produced by the base catalyzed decomposition of a corresponding pyrazoline (II) as defined hereinbefore, following the procedure of Masyuki Hamada described in Botyu-Kagaku 21, 22 (1956).

In particular the pyrazoline (II) may be produced by reacting a corresponding benzalacetophenone of formula (III):

(III)

with hydrazine or hydrazine hydrate; this reaction is suitably carried out under reflux conditions in a lower alkanol solvent, for example, ethanol.

Thereafter the product pyrazoline (II) is converted to the corresponding cyclopropane (I) by base catalyzed decomposition. Suitably the base catalyzed decomposition takes place at an elevated temperature, suitably 200°-220° C., preferably about 210° C. with an alkali metal hydroxide base, for example, sodium hydroxide.

The reaction is presumed to go through a radical intermediate as illustrated in the following equation:

It might have been expected that this reaction could not proceed in the case of hydroxyl substituents on the aromatic Ar radicals, but surprisingly the reaction proceeds efficiently. The reaction of Masyuki Hamada employed unsubstituted phenyl radicals as Ar or phenyl substituted by chloro or methoxy.

The process is illustrated schematically hereinafter:

trans/cis = 9/1
Yield > 80% iii) Polymers

The cyclopropanes (I) can be employed as monomers to produce cross-linkable polymers including homopolymers and copolymers.

The polymers are characterized by repeating units of formula (IV):

(IV)

wherein each ether linkage is in an ortho, meta or para-position.

The linking unit Ar is derived from an organic dihalide, more especially an activated dihalide in which the halogen atoms are readily displaced by phenolic hydroxyl.

Thus a homopolymer in this case may be prepared by the condensation of the hydroxy-substituted cyclopropane (I) with an activated dihalide to give the polymers as shown below with examples of different dihalides:

wherein each ether linkage is in an ortho, meta or para-position, Ar is a linking unit derived from an organic dihalide; and n is an integer of 2–200.

Suitably Ar is selected from divalent radicals of formula:

—CH$_2$— or —CO—.

X—Ar—X

Thus a homopolymer may be represented by the formula (V):

wherein Ar and n are as defined hereinbefore.

The copolymers of the invention are produced by copolymerization with a comonomer, especially a bisphenol or biphenol.

The copolymers may be represented by formula (VI):

wherein each ether linkage is in a position selected from ortho, meta or para; Ar is a linking unit derived from an organic dihalide; C$_m$ is a comonomer; p is an integer of 2–199, q is an integer of 1–198 and p+q is 3 to 200.

Suitably the comonomer C$_m$ is of formula (VII): wherein Ar$_1$ is selected from:

A specific example of a poly(ether sulfone) homopolymer is shown below:

Thus the homopolymers may be represented by the formula:

The following reaction scheme illustrates production of copolymers in accordance with the invention.

n/m = 1/4

Ar

Similarly a polyformal copolymer with BPA is shown below.

and a copolyester with BPA is shown below

+

Polycarbonates and epoxy resins can also be synthesized.
When these polymers are heated they undergo an exothermic reaction very similar to that which occurs when the acetylene containing polymers are heated.

DETAILED DESCRIPTION OF DRAWINGS

Figure 1:
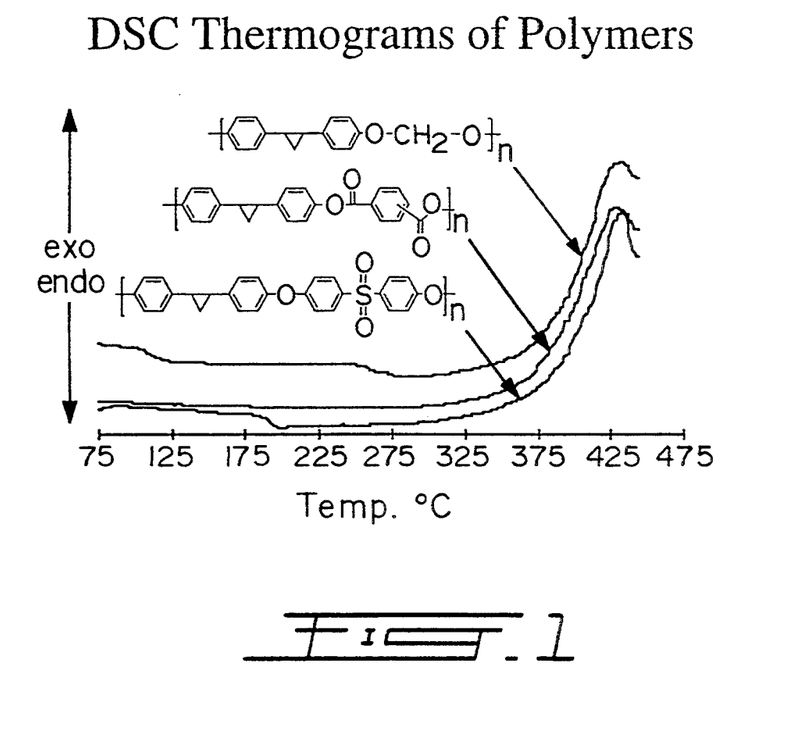
FIG. 1 is a DSC thermogram of certain polymers of the invention.
Figure 2:
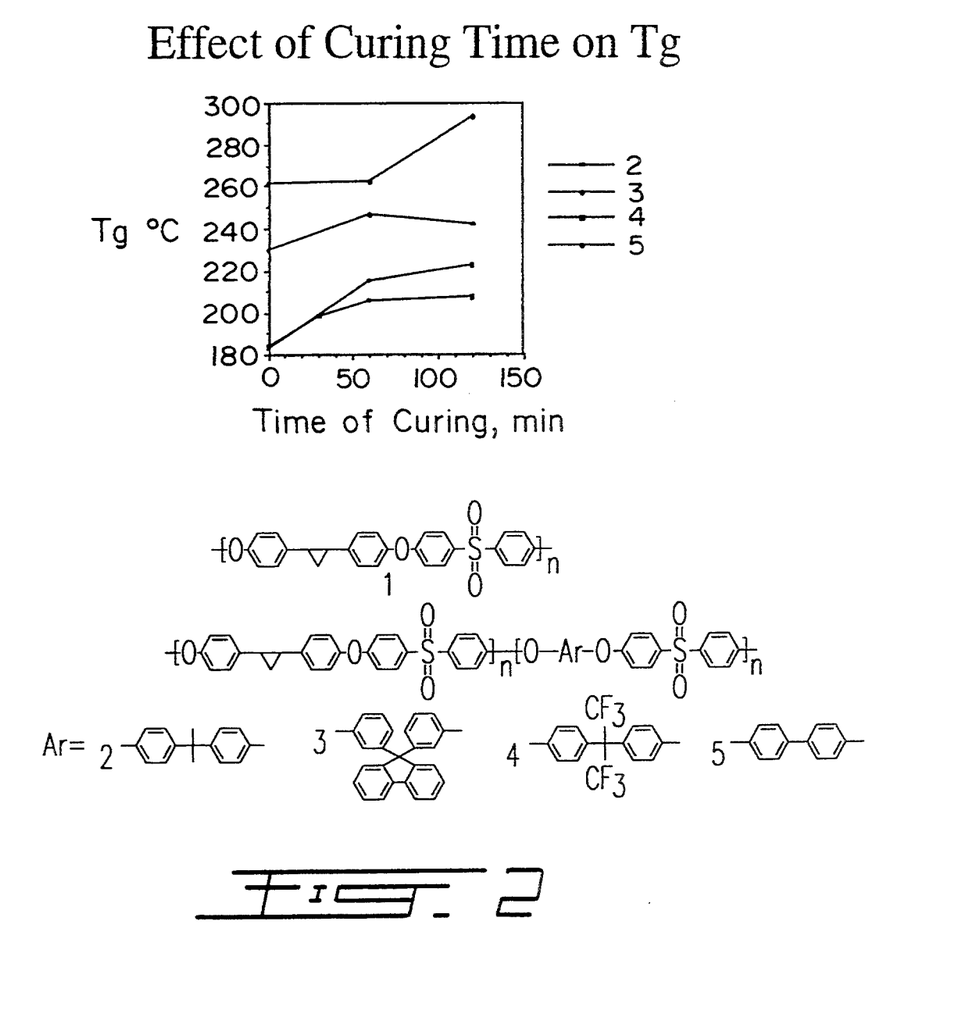
FIG. 2 illustrates the effect of curing time on $T_g$ for different polymers of the invention.

From FIG. 1 it can be seen that the glass transition temperatures of the polymers of the invention increases after heating, which signifies that cross-linking has taken place.

Figure 3:
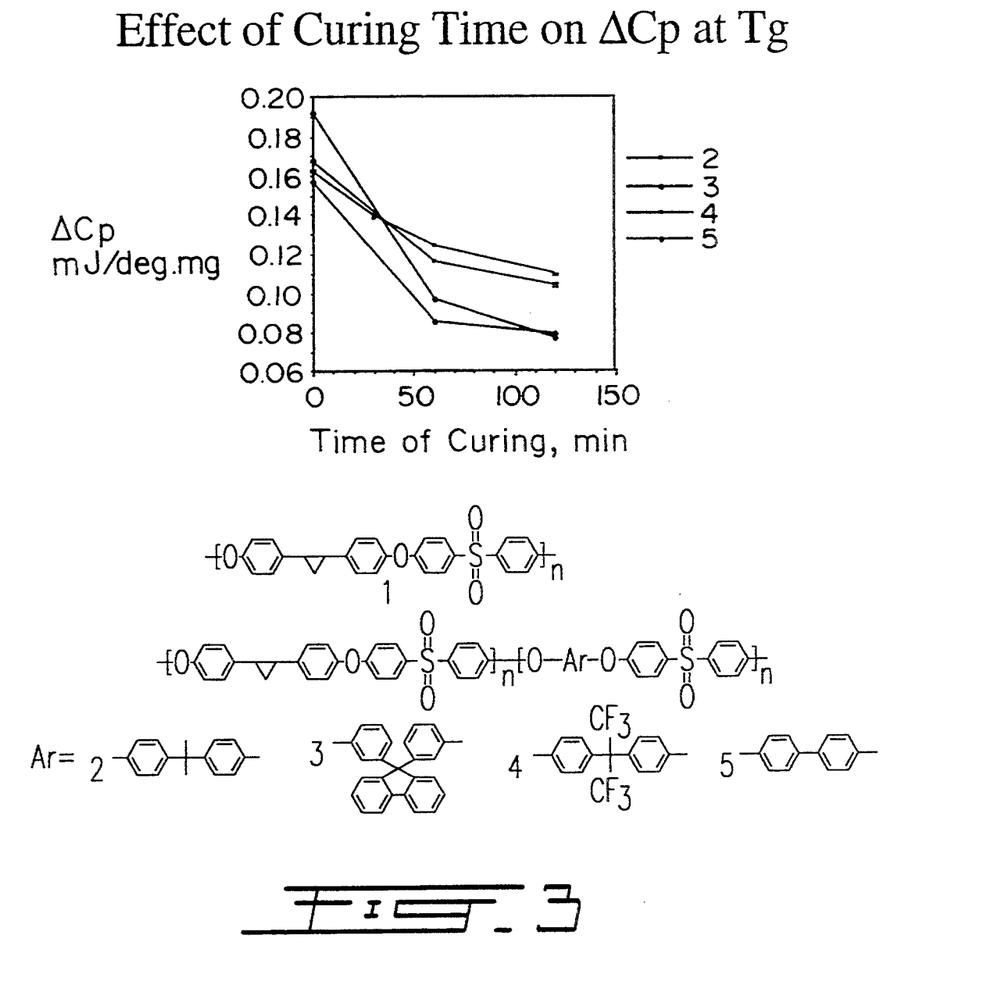
FIG. 3 illustrates the effect of curing time on $\Delta C_p$ at $T_g$ for different polymers of the invention.

FIG. 3 demonstrates that the solubility of polymers of the invention changes after heating, and that polymers having large concentrations of the cyclopropane moieties become completely insoluble and swelling occurs.

Figure 4:
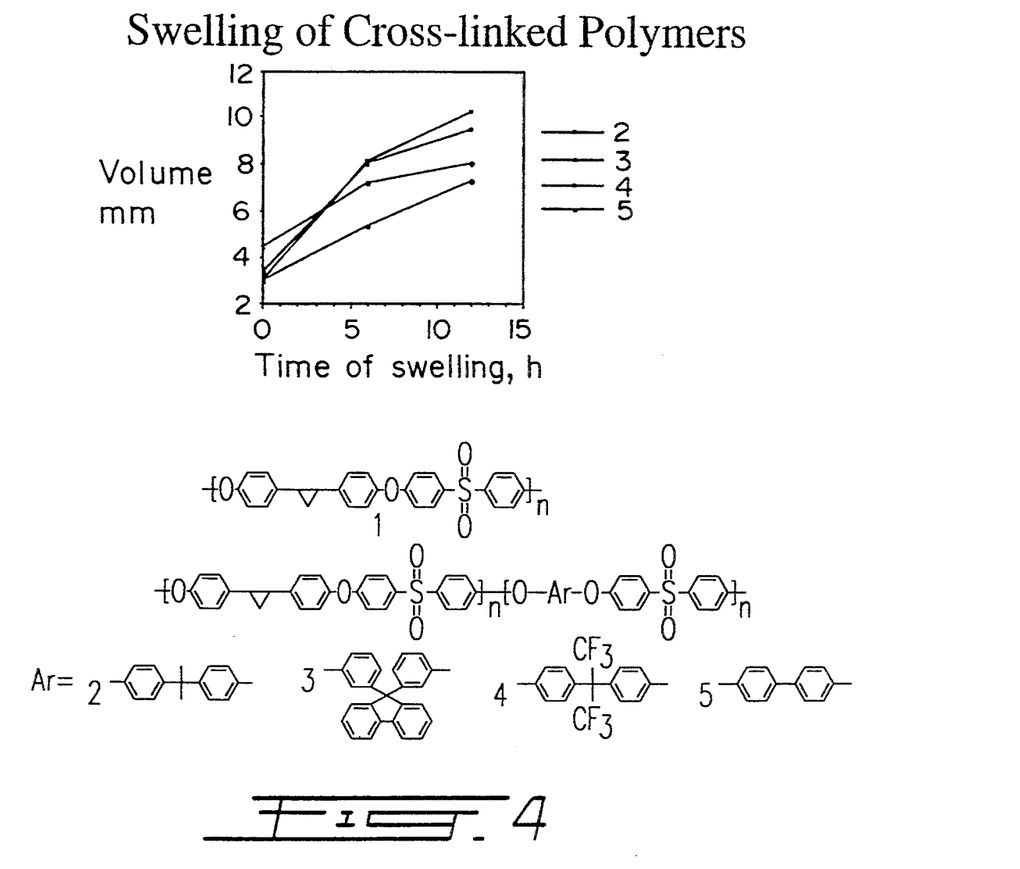
FIG. 4 illustrates the swelling of cross-linked polymers of the invention.
Figure 5:
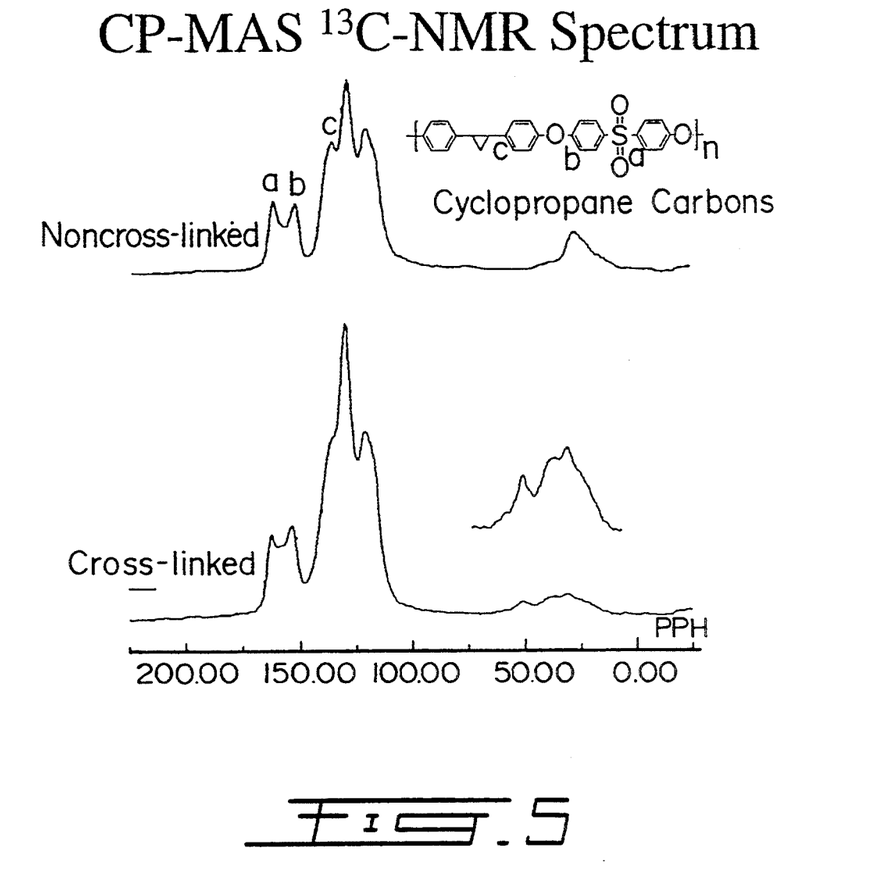
FIG. 5 shows the CP-MAS $^{13}$C-NMR spectrum of a polymer of the invention.

FIG. 4 demonstrates that using solid state $^{13}$C-NMR the course of the cross-linking reaction can be monitored by the disappearance of cyclopropane groups.

EXAMPLES

EXAMPLE 1

4,4'-dihydroxychalcone.

It was synthesized according to the method previously described (T. A. Geissman and R. O. Clinton, J. Am. Chem. Soc., 68, 697, (1946); R. G. Christiansen, R. R. Brown, A. S. Hay, A. Nickon and R. B. Sandin, J. Am. Chem. Soc., 77, 948, (1955), mp 203°–205° C.; $^1$H NMR (DMSO-d$_6$) δ6.75–6.95 ( two d, 4H), 7.60–7.75 (d, 2H), 7.70 (s, 2H), 7.98–8.06 (d, 2H), 10.22 (s, 2H).

EXAMPLE 2

3,4'-dihydroxychalcone

It was synthesized according to the method used in example 1. mp 242°–245° C.; $^1$H NMR (DMSO-d$_6$)

δ6.82–7.32 (m, 6H), 7.58–7.88 (q, 2HO, 8.10 (d, 2H), 10.00 (s, 2H).

EXAMPLE 3 trans-3,5-Bis (p-hydroxyphenyl)-2-pyrazoline

To a solution of 30.7 g of 4,4'-dihydroxychalcone in 300 mL of ethanol 30 mL of hydrazine monohydrate was added. The resulting solution was refluxing for one and half hours. Ice water was then added. The precipitate was collected, dried and crystallized from acetic acid, yield >90%; mp 183°–185° C.; $^1$H NMR (CD$_3$OD) δ2.90–3.45(octet, 2H), 4.70–4.80 (t, 1H), 6.74–6.83 (two d, 4H), 7.18–7.22 (d, 2H), 7.51–7.56 (d, 2H). MS m/z 254 (M+, 100), 161 (30), 134 (15), 120 (20).

EXAMPLE 4 trans-3(4-hydroxyphenyl)-5(3-hydroxyphenyl)-2-pyrazoline

It was synthesized by the method used in example 3, yield >90%; mp 234°–235° C.; $^1$H NMR (CD$_3$OD) δ2.71–3.42 (octet, 2H), 4.63–4.75 (t,1H), 6.62–7.18 (m, 6H), 7.45–7.50 (d,2H). MS m/z 254 (M+, 100), 161 (66), 134 (14), 120(16).

EXAMPLE 5 trans-3-phenyl-5(4-hydroxyphenyl)-2-pyrazoline

It was synthesized by the method used in example 3 using 22.8 g of 4-hydroxychalcone and 22.3 mL of hydrazine monohydrate, yield >90%; mp 139°–140° C.; 1H NMR (DMSO) δ2.71–3.42 (octet, 2H), 4.66–4.78 (sextet, 1H), 6.69–6.72 (d, 2H), 7.12–7.46 (m, 5H), 7.59–7.62 (d, 2H). MS m/z 238 (M+, 100), 145 (13), 120 (15).

EXAMPLE 6 trans-3(4-hydroxyphenyl)-5-phenyl-2-pyrazoline

It was synthesized by the method used in example 3, yield >90%; mp 105°–109° C.; $^1$H NMR (DMSO) δ2.69–3.44 (octet, 2H), 4.70–4.81 (sextet, 1H), 6.74–6.78 (d, 2H), 7.24–7.38 (m, 5H), 7.43–7.47 (d, 2H); MS m/z 238 (M+, 100), 161 (53), 134 (10), 129 (4), 120 (6), 119 (9).

EXAMPLE 7 trans-1,2-bis (p-hydroxyphenyl) cyclopropane

1.0 g of trans-3,5-Bis (p-hydroxyphenyl)-2-pyrazoline was mixed with 1.0 g of powdered sodium hydroxide. The mixture was heated to 250° C. under nitrogen and the decomposition proceeded for 30 min. The cooled reaction product was dissolved in water and then neutralized with hydrochloric acid and extracted with ether. The ether layer was washed with water to remove the salt. Removal of the ether left the product which was crystallized from acetic acid, mp 190°–191° C.; $^1$H NMR (DMSO-d$_6$) δ1.1.16–1.22 (t,2H), 1.80–1.98 (t, 2H), 6.60–6.70 (d, 4H), 6.90–6.96 (d, 4H), 9.15 (s, 2H). MS m/z 226 (M+, 100), 131 (15), 121 (45), 10.7 (20)

EXAMPLE 8 trans-1-(3-hydroxyphenyl)-2-(p-hydroxyphenyl)cyclopropane

It was synthesized by the method used in example 7, mp 123°–125° C.; $^1$H NMR (DMSO-d6) δ1.23–1.30 (t, 2H), 1.94–2.07 (m, 2H), 6.50–7.06 (m, 8H), 9.16 (s, 1H), 9.2S (s, 1H). MS m/z 226 (M+, 100), 131 (31), 120 (16), 107 (27).

EXAMPLE 9 trans-1-(4-hydroxyphenyl)-2-(phenyl) cyclopropane

It was synthesized by same procedure used in example 7 using 1.0 g of trans-3-phenyl-5(4-hydroxyphenyl)-2-pyrazoline and 0.5 g of sodium hydroxide, mp 78°–79° C.; 1H NMR (acetone-d$_6$) δ1.31–1.39 (t,2H), 2.04–2.10 (m, 2H), 6.73–6.78 (d, 2H), 7.00–7.04 (d, 2H), 7.17–7.26 (m, 5H), 8.12 (s, 1H); MS m/z 210 (M+, 100), 107 (20), 115 (30), 131 (17).

POLYMER PREPARATION

Poly(ether sulfone)s

EXAMPLE 10

Homopolymer from trans-1,2-bis(4-hydroxyphenyl)cyclopropane

A mixture of 0.003 mol (0.6788 g) of trans-1,2-bis(4-hydroxyphenyl)cyclopropane 0.774 g of K$_2$CO$_3$ and 0.003 mol (0.7628 g) of 4,4'-difluorodiphenylsulphone in 4 mL of toluene and 8 mL of N,N'-dimethylacetamide (freshly purified) was heated with stirring under nitrogen atmosphere with azeotropic removal of water for 3 hours. Some toluene was bled continuously from the Dean-Stark trap until the temperature rose to 155° C. The reaction mixture appears lightly coloured and is maintained at this temperature for 2 h. At this time the reaction was assumed to be complete. The reaction mixture was cooled to 100° C. and diluted with 5 mL of N,N'-dimethylacetamide and filtered. The filtrate was neutralized with acetic acid and coagulated into methanol. The precipitate was filtered and washed with methanolic water and finally with water. It was then boiled in distilled water for 1 hour to remove any trapped salts, filtered and dried in a vacuum oven at 80° C.; yield>90%. $^1$H-NMR (200 MHz, DMSO); proton, shift (ppm): a, d7.89 (d, 4H); d, d7.22 (d, 4H); b,c,d7.04 (m, 8H); f,d2.23 (t, 2H), e, d1.45(t, 2H).

Copolymers

A mixture of trans-1,2-bis(4-hydroxyphenyl)cyclopropane, the other bisphenol, 0.774 g of K$_2$CO$_3$ and 0.003 mol (0.7628 g) of 4,4'-difluorodiphenylsulphone. 4 mL of toluene and 8 mL of N,N'-dimethylacetamide (freshly purified) was treated as in example 10 for the synthesis of the homopolymer.

| Ar | Example | Tg (uncured) °C. DSC | Tg (cured) °C.[b] | η$_{inh}$[c] | TGA[d] N$_2$ (−5%) |
|---|---|---|---|---|---|
| nil | 10 | 189 | ND | 0.35 | 450 |
|  -C(CH$_3$)- diphenyl | 11 | 184 | 207 | 0.41 | 438 |
| fluorenyl bis-phenyl | 12 | 261 | 293 | 0.56 | 449 |
| -C(CF$_3$)$_2$- diphenyl | 13 | 183 | 222 | 0.60 | 428 |

-continued

| Ar | Example | Tg (uncured) °C. DSC | Tg (cured) °C.[b] | $\eta_{inh}$[c] | TGA[d] $N_2$ (−5%) |
|---|---|---|---|---|---|
|  | 14 | 230 | 246 | 0.62 | 451 |

[a]DSC, heating at 10° C./min.
[b]After curing for 2 h at 350° C. under $N_2$.
[c]5 g/dl in CHCl₃ at 25° C.
[d]TGA, heating at 10° C./min.
[e]GPC, based on polystyrene standards.

Polyformals

EXAMPLE 16

Homopolymer from trans-1,2-bis(4hydroxyphenyl))cyclopropane

A mixture of 2.26 g of trans-1,2-bis(4-hydroxyphenyl)cyclopropane, 0.0225 g of p-t-butylphenol, 3.09 mL of reagent grade methylene chloride, and 5 mL of NMP was stirred under nitrogen until a homogeneous solution was obtained. At this point 0.849 g of NaOH pellets was added and the mixture exothermed to 37° C. The mixture was placed in a 90° C. oil bath and the solution was refluxed for 2 h, after which the solution was cooled and diluted with NMP. The mixture was allowed to cool to room temperature and the white solid (NaCl) was removed by filtration. The polymer was isolated by a reverse precipitation. This procedure involved the addition of 50:50 (v/v) MeOH:acetone mixture to the polymer solution while stirring. The resulting solid was filtered and dried in a 75° C. vacuum oven; yield >90%. ¹H-NMR (CDCl3). proton, shift (ppm): a, d 7.00 (s, 8H), b, d5.65 (s, 2H), c, d2.00 (t, 2H), d, d1.30 (t, 3H).

Copolymers

Copolymers with BPA were made by the procedure as described in example 16.

| Example | BPA/Δ | dL/g $\eta_{inh}$[a] | Mw/Mn[b] DSC | Tg(°C.)[c] $N_2$/Air | TGA[d] | Solubility |
|---|---|---|---|---|---|---|
| 16 | 0 | 0.58 | | 98.5 | 433/411 | DMAc |
| 17 | 3/7 | 0.40 | 36253/21632 | 92.9 | 438/416 | CHCl₃ |
| 18 | 1/1 | 0.45 | 35169/20576 | 95.0 | 444/405 | CHCl₃ |
| 19 | 7/3 | 0.40 | 33138/18294 | 95.3 | 433/411 | CHCl₃ |

[a]5 g/dl in ChCl₃ at 25° C. or in DMAc at 50° C.
[b]GPC, based on polystyrene standards.
[c]DSC heating at 10° C./min.
[d]TGA, heating at 10° C./min.

The glass transition temperatures of these polymers increase significantly when heated as shown below.

| n/m | Curing Time (min) | Tg (°C.) | ΔCp mJ/deg.mg |
|---|---|---|---|
| 0 | 0 | 98.5 | 0.205 |
| | 30 | 166.9 | 0.026 |
| | 120 | ND | — |
| 3/7 | 0 | 92.9 | 0.275 |
| | 60 | 138.0 | 0.015 |
| | 120 | ND | — |
| 1/1 | 0 | 95.0 | 0.222 |
| | 60 | 126.0 | 0.104 |
| | 120 | 128.0 | 0.061 |
| 7/3 | 0 | 95.3 | 0.334 |
| | 60 | 115.0 | 0.168 |
| | 120 | 116.0 | 0.084 |

*Tg and Cp were measured in DSC with heating rate 10° C./min

Polyesters

A solution of 0.0025 mole of bisphenol(s) and 0.2 g of sodium hydroxide in 15 ml. of water was prepared in a blender. A second solution containing 0.0025 mole of acid chloride(s) in 7.5 mL of chloroform was prepared in a beaker. A solution of 0.15 g Duponol ME (Sodium lauryl sulfate) detergent in 1.5 mL of water was added to the slowly stirred aqueous solution in the bender, and the blender was run at maximum speed. The acid chloride solution was added as rapidly as possible and the emulsion so formed and was stirred for five minutes. The reaction mixture was filtered off, the polymer was washed well with water to remove occluded and detergent, and dried.

| Example | m/n | $\eta_{inh}^a$ dL/g | $Tg^b$ (°C.) | TGA(°C.)$^c$ $N_2$/Air | solubility |
|---|---|---|---|---|---|
| 20 | 0 | — | — | 435/420 | — |
| 21 | 1/1 | 1.38 | 208.2 | 426/421 | DMAc |
| 22 | 4/1 | 1.51 | 208.0 | 464/430 | DMAc |

$^a$5 g/dl in DMAc at 50° C.
$^b$DSC, heating at 10° C./min.
$^c$TGA, heating at 10° C./min.

The copolymers on curing show increases in Tg as shown below. They also become insoluble on heating.

| m/n | Curing time (min) | Tg (°C.) | ΔCp mJ/deg.mg |
|---|---|---|---|
| 1/1 | 0 | 208.2 | 0.191 |
|  | 60 | 230. | 0.011 |
|  | 120 | ND | ND |
| 4/1 | 0 | 208 | 0.104 |
|  | 60 | 220 | 0.082 |
|  | 120 | 236 | 0.031 |

*Tg and ΔCp were measured in DSC with heating rate 10° C./min. Curing T = 350° C.

I claim:

1. A cyclopropane of formula (I):

wherein $R_1$ and $R_2$ are selected from H or OH, at least one of $R_1$ and $R_2$ being o, m or p-OH.

2. A cyclopropane of formula (I), according to claim 1, wherein $R_1$ and $R_2$ are both OH.

3. A cyclopropane according to claim 2, wherein $R_1$ and $R_2$ are both p-OH.

4. A cyclopropane according to claim 2, wherein $R_1$ is m-OH and $R_2$ is p-OH.

5. A cyclopropane of formula (I), according to claim 1, wherein $R_1$ is OH and $R_2$ is H.

6. A cyclopropane according to claim 5, wherein $R_1$ is p-OH.

7. A pyrazoline of formula (II):

wherein $R_1$ and $R_2$ are selected from H or OH, at least one of $R_1$ and $R_2$ being o, m or p-OH.

8. A cyclopropane group-containing homopolymer of formula:

wherein each ether linkage is in an ortho, meta or para position, Ar is a linking unit derived from an organic dihalide; and n is an integer of 2–200.

9. A homopolymer according to claim 8, wherein Ar is selected from divalent radicals of formula:

-continued or

—CH$_2$— or —CO—.

10. A homopolymer according to claim 8, of formula (V):

wherein Ar and n are as defined in claim 8.

11. A cyclopropane group-containing copolymer of formula (VI):

wherein each ether linkage is in a position selected from ortho, meta or para; Ar is a linking unit derived from an organic dihalide; $C_m$ is a comonomer; p is an integer of 2–199, q is an integer of 1–198 and p+q is 3 to 200.

12. A copolymer of formula (VI), as defined in claim 11, wherein Ar is selected from divalent radicals of formula:

-continued or

—CH$_2$— or —CO—.

13. A copolymer of formula (VI), as defined in claim 12, wherein said comonomer $C_m$ is derived from a bis-phenol or a biphenol.

14. A copolymer of formula (VI), as defined in claim 12, wherein said comonomer $C_m$ is of formula (VII):

—O—Ar$_1$—O—  (VII)

wherein Ar$_1$ is selected from:

or wherein R$_1$ and R$_2$ are independently selected from alkyl of 1 to 4 carbon atoms.

* * * * *